United States Patent [19]

Grollier et al.

[11] Patent Number: 4,804,385
[45] Date of Patent: Feb. 14, 1989

[54] PROCESS FOR DYEING KERATINOUS FIBRES WITH 5,6-DIHYDROXY-INDOLE COMBINED WITH AN IODIDE AND DYEING COMPOSITION EMPLOYED

[75] Inventors: Jean F. Grollier, Paris; Didier Garoche, Levallois-Perret, both of France

[73] Assignee: L'Oreal, Paris, France

[21] Appl. No.: 4,496

[22] Filed: Jan. 20, 1987

[30] Foreign Application Priority Data

Jan. 20, 1986 [LU] Luxembourg ............................ 86256

[51] Int. Cl.$^4$ ................................................ A61K 7/13
[52] U.S. Cl. ............................................ 8/423; 8/406; 8/634
[58] Field of Search .................... 8/404, 405, 406, 423, 8/634

[56] References Cited

U.S. PATENT DOCUMENTS 1,677,508 7/1928 Windgradoff et al. ................. 8/405
2,934,396 4/1960 Charle et al. ............................ 8/593
4,208,183 6/1980 Grollier et al. ......................... 8/609

FOREIGN PATENT DOCUMENTS 1469739 1/1969 Fed. Rep. of Germany .
2028818 12/1970 Fed. Rep. of Germany .
2028818 12/1970 Fed. Rep. of Germany .
1133594 11/1956 France .
1166172 6/1958 France .
1264707 5/1961 France .
1365276 5/1964 France .
2486395 1/1982 France .
2132642 7/1984 United Kingdom .

Primary Examiner—Paul Lieberman
Assistant Examiner—Linda D. Skaling
Attorney, Agent, or Firm—Cushman, Darby & Cushman

[57] ABSTRACT

The invention relates to a plural stage process for dyeing keratinous fibers wherein a composition (A) comprising, in a medium suitable for dyeing, 5,6-dihydroxyindole and iodide ions, is applied to the hair, the application of said composition (A) being preceded or followed by the application of a composition (B) comprising hydrogen peroxide.

30 Claims, No Drawings

PROCESS FOR DYEING KERATINOUS FIBRES WITH 5,6-DIHYDROXY-INDOLE COMBINED WITH AN IODIDE AND DYEING COMPOSITION EMPLOYED

The present invention relates to a new process for colouring keratinous fibres, especially human, with 5,6-dihydroxyindole and to compositions employed in this process.

It is well known that the natural biosynthesis of eumelanins from tyrosine is carried out in several stages. One of them consists in the formation of 5,6-dihydroxyindole which oxidizes to give a pigment which is one of the main constituents of eumelanin.

Many processes for dyeing hair which employ 5,6-dihydroxyindole or some of its derivatives have already been proposed in the past.

Thus, in French Pat. No. 1,166,172, a solution of 5,6-dihydroxyindole with an acid pH is applied to the hair for 5 to 60 minutes, and without rinsing and after wringing, the colour is revealed using an oxidizing agent which may especially be hydrogen peroxide.

In French Pat. No. 1,133,594, an alkaline solution of 5,6-dihydroxyindole containing, if required, an oxidizing agent or an oxidation catalyst, is applied to the hair. Different oxidizing agents, including hydrogen peroxide and oxidation catalysts, such as cupric chloride, are provided for.

According to this process, it is also possible to operate in two stages by following the application of 5,6-dihydroxyindole in an alkaline medium by a rinsing and a revealing with an oxidation catalyst.

In French Patent Application No. 2,536,993, a process for dyeing in several stages separated by rinsings and consisting in applying, in a first stage, a metal salt solution with an alkaline pH and, in another stage, a 5,6-dihydroxyindole solution has also been recommended.

These two stages are, after rinsing or shampooing, followed or otherwise by an application of hydrogen peroxide to adjust the final shade by lightening.

These processes of the prior art have different drawbacks insofar as they lead either to shades which are not very strong despite long exposure time, or to the production of strong shades which require a long exposure time and leading to a surface dyeing which is not very fast. The use of some metal salts of groups III to VIII of the periodic classification, the harmlessness of which has not always been demonstrated, may lead, under the conditions of use, to a modification of the cosmetic or mechanical properties of hair.

Moreover, compositions based on 5,6-hydroxyindole have problems of stability during storage, especially in an alkaline medium.

The Applicant Company has now discovered, and this forms the subject of the invention, means which enable strong shades to be obtained with 5,6-dihydroxyindole with short exposure times without using any metal or metal salt of groups III to VIII and which employ a solution of 5,6-dihydroxyindole with an acid pH.

Another subject of the invention consists of compositions employed in this process and "kits" or dyeing outfits containing several components which employ these different compounds.

Other subjects of the invention will be apparent on reading the description and the examples which follow.

The process for dyeing keratinous fibres, preferably human, according to the invention is characterized essentially in that at least one composition (A) containing, in a medium suitable for dyeing, 5,6-dihydroxyindole in combination with iodide ions, at a pH of between 2 and 7 and preferably between 3.5 and 7 is applied to these fibres, the application of this composition (A) being preceded or followed by the application of a composition (B) which contains, in a medium suitable for dyeing, hydrogen peroxide at a pH of between 2 and 7 and preferably between 2 and 5, the application of the compositions (A) and (B) being separated, if required, by a rinsing stage.

The iodide ion is preferably an alkali metal or alkaline-earth metal or ammonium iodide and more particularly potassium iodide.

The process according to the invention is preferably implemented by applying, in a first stage, the composition (A) containing iodide ions in the form of alkali metal or alkaline-earth metal or ammonium iodide and 5,6-dihydroxyindole, and then the composition (B) containing hydrogen peroxide.

The process is preferably applied to the dyeing of hair, and especially living human hair, in which case the medium employed must be cosmetically acceptable.

According to a preferred embodiment, the fibres are rinsed between the two stages, which enables, among other things, the staining of the scalp to be avoided, when the composition is used for the dyeing of human hair.

When the process is implemented without rinsing the fibres between the two stages, the exposure time may be reduced.

In the compositions used in the process according to the invention, 5,6-dihydroxyindole is generally present in proportions of between 0.01 and 5% by weight, preferably between 0.03 and 3% by weight relative to the total weight of the composition. The proportion of iodide in the compositions applied during the process according to the invention is between 0.007 and 4% by weight expressed as $I^-$ ions and preferably between 0.03 and 2.5% relative to the total weight of the composition.

The 5,6-dihydroxyindole/$I^-$ weight ratio is preferably between 0.05 and 10 and more particularly between 0.5 and 2.

The hydrogen peroxide concentration in the hydrogen peroxide compositions used is between 1 and 40 volumes, preferably between 2 and 20 volumes, and more particularly between 3 and 15 volumes.

The process is implemented allowing exposure times, for the different compositions applied in each of the different stages of the process, of between 10 seconds and 45 minutes and preferably of the order of 2 to 25 minutes and more particularly of the order of 2 to 15 minutes.

The Applicant Company has observed that the process employed enabled colourings which are both rapid and strong, which penetrate well into the fibres, and especially human keratinous fibres such as hair, without the risk of degrading the hair and which have a good resistance to washing and to light to be obtained.

It has also observed that hair dyed several times following its regrowth with the process and the composition according to the invention, was softer, shinier and had good mechanical properties compared with hair dyed by employing processes and compositions of the prior art.

Colourings which are relatively intense are obtained in fairly short times, of the order of 5 to 15 minutes.

The compositions used for the implementation of the process according to the invention, may be present in diverse forms, such as more or less thickened or gellified liquids, creams, emulsions, foams or other forms suitable for carrying out dyeing.

The dyeing compositions intended to be used in the process according to the invention, containing 5,6-dihydroxyindole in combination with iodide ions, generally comprise an aqueous medium, consisting of water or a water/solvent(s) mixture, or an anhydrous solvent medium, the solvent(s) being preferably chosen from organic solvents such as ethyl alcohol, propyl or isopropyl alcohol, tert-butyl alcohol, ethylene glycol, monomethyl, monoethyl and monobutyl ethers of ethylene glycol, ethylene glycol monoethyl ether acetate, propylene glycol, monomethyl ether of propylene glycol and dipropylene glycol and methyl lactate.

The preferred solvents are ethyl alcohol and propylene glycol.

When the medium is aqueous, the composition has a pH of between 2 and 7 and preferably between 3.5 and 7.

It is also possible to store the 5,6-dihydroxyindole and/or the iodide in a medium consisting of anhydrous solvents, and to mix this (these) medium (media) with an aqueous medium at the time of use.

A solvent containing less than 1% water is called an anhydrous solvent.

When the medium consists of a water/solvent(s) mixture, the solvents are present in concentrations preferably between 0.5 and 75%, especially between 2 and 50% and more particularly between 2 and 20% by weight relative to the total weight of the composition.

When the medium containing the 5,6-dihydroxyindole is aqueous, its pH is between 2 and 7 and preferably between 3.5 and 7.

The compositions used according to the invention may also contain fatty amides such as mono- and diethanolamides of acids derived from coconut, lauric acid and oleic acid, at concentrations of between 0.05 and 10% by weight.

These compositions may also contain anionic, cationic, non-ionic or amphoteric surfactants or their mixtures. These surfactants are preferably used in proportions of between 0.1 and 50% by weight relative to the total weight of the composition and advantageously between 1 and 20% by weight.

The compositions defined above may be thickened with thickening agents such as sodium alginate, gum arabic, guar gum, biopolymers such as xanthan gum or scleroglucans, cellulose derivatives such as methyl cellulose, hydroxyethyl cellulose, hydroxypropylmethyl cellulose, sodium salt of carboxymethyl cellulose and acrylic acid polymers. Inorganic thickening agents such as bentonite may also be used. These thickeners are used alone or in mixture and are preferably present in proportions of between 0.1 and 5% by weight relative to the total weight of the composition and advantageously between 0.5 and 3%.

The alkalinizing agents which can be used in these compositions may especially be amines such as alcanolamines, alkylamines, alkali metal or ammonium hydroxides or carbonates. The acidifying agents which can be used in the compositions according to the invention may be chosen from lactic acid, acetic acid, tartaric acid, phosphoric acid, hydrochloric acid and citric acid.

It is possible to use any other alkalinizing or acidifying agent.

It is possible to add, if required, to each of the compositions a swelling agent for the keratinous fibre such as, for example, urea.

When the composition is used in the form of a foam, it may be packaged under pressure in an aerosol device in the presence of a propellant and at least one foam generator. The foam generators may be anionic, cationic, non-ionic or amphoteric foaming polymers or the surfactants defined above.

The compositions employed in the process according to the invention may additionally contain different adjuvants such as perfumes, sequestrants, film-forming agents, treatment agents, dispersants, conditioners, preservatives or opaqueing agents.

The invention also relates to a composition intended to be used in the dyeing of keratinous fibres, preferably human, containing, in a medium suitable for dyeing, 5,6-dihydroxyindole and iodide ions in the preferred form of an alkali metal or alkaline-earth metal or ammonium iodide. Surprisingly, such a composition is particularly stable during storage.

With a view to implementing the process according to the invention, the compositions may be packaged in devices containing several compartments also called "kits" or dyeing outfits containing all the components intended to be applied, for one and the same dyeing operation, to keratinous fibres in successive applications, with or without premixing. Such devices are known in themselves and may comprise a first compartment containing the composition which contains 5,6-dihydroxyindole in the presence of iodide ions in a medium suitable for dyeing, and in a second compartment, a hydrogen peroxide solution at a pH of between 2 and 7 and preferably between 2 and 5.

If the medium containing 5,6-dihydroxyindole consists of an anhydrous solvent, mixing is carried out, before use, with an aqueous support suitable for dyeing, possibly present in a third compartment. The composition containing 5,6-dihydroxyindole and iodide ions in an anhydrous medium may also be applied directly to keratinous fibres which are wet.

When the medium suitable for dyeing is aqueous, the composition of the first compartment preferably has a pH of between 2 and 7 and preferably between 3.5 and 7.

According to another embodiment, the "kit" or the dyeing outfit comprises a first compartment containing a composition which contains iodide ions in a medium suitable for dyeing, a second compartment containing a composition which contains 5,6-dihydroxyindole in a medium suitable for dyeing and a third compartment containing a 1 to 40 volume hydrogen peroxide composition at a pH of between 2 and 7, and preferably between 2 and 5, the composition contained in the second compartment being intended to be mixed with the contents of the first compartment at the time of use.

When the media present in the first and second compartments are aqueous, they preferably have a pH of between 2 and 11 for the first and between 2 and 7 and especially 3.5 and 7 for the second.

The devices may be equipped with means for mixing at the time of use which are known in themselves and which may be packaged in an inert atmosphere.

The processes according to the invention and the corresponding compositions may be used for dyeing natural or already dyed hair, permed or otherwise, or uncurled, or strongly or slightly bleached and possibly permed hair.

It is also possible to use them for dyeing furs or wool.

The following examples are intended to illustrate the invention without implied limitation.

EXAMPLE 1

The colouring of natural white hair is carried out by applying successively two compositions without intermediate rinsing.

The hair is carefully impregnated for three minutes with the following composition:
5,6-dihydroxyindole: 2 g
potassium iodide: 3 g
ethyl alcohol: 10 g
sodium alkyl ether sulphate at a concentration of 0.6 meq/g: 20 g
Water qs: 100 g.

The pH is 5.

A 10 volume hydrogen peroxide solution with a pH of 4 is applied consecutively and without rinsing, rubbing the hair for two minutes.

The hair is rinsed thoroughly. A dark grey colour is obtained.

EXAMPLE 2

The colouring of permed white hair is carried out by applying successively two compositions without intermediate rinsing.

The hair is carefully impregnated for three minutes with the following composition:
5,6-dihydroxyindole: 1 g
potassium iodide: 3 g
ethyl alcohol: 10 g
sodium alkyl ether sulphate at a concentration of 0.6 meq/g: 20 g
water qs: 100 g.

The pH is 5.1.

The hair is exposed for 10 minutes and rinsed thoroughly. A golden chestnut brown colour is obtained.

EXAMPLE 3

The colouring of permed white hair is carried out by applying successively two compositions without intermediate rinsing.

The hair is impregnated for 5 minutes with the following composition:
5,6-dihydroxyindole: 1 g
ammonium iodide: 1 g
ethyl alcohol: 10 g
water qs: 100 g.

The pH is 4.5.

The hair is wrung and, without rinsing, a 10 volume hydrogen peroxide solution (pH=4) is applied rubbing the hair for 5 minutes. The hair is rinsed and a black colour is obtained.

EXAMPLE 4

The colouring of natural white hair is carried out in the same way as in Example 3, but replacing ammonium iodide with 1 g of sodium iodide. Under the same conditions as in Example 3, a medium grey colour of hair is obtained.

The composition used in the first stage of the process has a pH of 5.8.

EXAMPLE 5

The colouring of 90% white hair is carried out by applying successively two compositions without intermediate rinsing.
5,6-dihydroxyindole: 2 g
potassium iodide: 2 g
ethyl alcohol: 10 g
sodium lauryl ether sulphate/ethylene oxide condensate with 2 moles of ethylene oxide: 4.2 g AS
spontaneous pH: 6
water qs: 100 g.

Aerosol Packaging above mixture 90 g
propellants: Fréons 114/12 (43/57) 10 g.

The hair is carefully impregnated for 4 minutes with the composition in the form of a foam dispensed from an aerosol packaging.

A 12.5 volume hydrogen peroxide composition with a pH of 2 is applied consecutively and without rinsing, rubbing the hair for 3 minutes. After rinsing and drying, a black colour is obtained.

EXAMPLE 6

The colouring of natural 90% white hair is carried out by applying successively two compositions without intermediate rinsing.
5,6-dihydroxyindole: 1.7 g
potassium iodide: 3.5 g
ethyl alcohol: 10 g
sodium lauryl ether sulphate/ethylene oxide condensate with 2 moles of ethylene oxide: 7 g AS
spontaneous pH: 6
water qs: 100 g.

Aerosol Packaging above mixture: 90 g
propellants: Freons 114/12 (43/57): 10 g.

The hair is impregnated for 4 minutes with the composition in the form of a foam dispensed from an aerosol packaging.

A 15 volume hydrogen peroxide composition with a pH of 4 is applied consecutively and without rinsing, rubbing the hair for 3 minutes. After rinsing and drying, a natural ash chestnut brown colour is obtained.

EXAMPLE 7

The colouring of 90% white hair is carried out by applying successively, and rinsing between the two applications, a composition A as follows:
5,6-dihydroxyindole: 3 g
potassium iodide: 2 g
ethyl alcohol: 10 g
xanthan gum sold under the name "RHODOPOL 23 SC" by RHONE POULENC: 1 g
glycoside alkyl ether sold at 60% AS concentration under the name "TRITON CG 110" by SEPPIC: 5 g AS
spontaneous pH: 6.5
water qs: 100 g.

The hair is exposed for 15 minutes. After rinsing with water, a composition B, containing 12.5 volume hydrogen peroxide at pH 5 is applied, rubbing the hair for 5 minutes.

After rinsing the hair with water and drying, a black colour is obtained.

EXAMPLE 8

The colouring of 90% white hair is carried out by applying successively, and rinsing between the two applications, a composition A as follows:

5,6-dihydroxyindole: 2.5 g
potassium iodide: 2 g
ethyl alcohol: 10 g
guar gum sold under the name "JAGUAR HP 60" by CELANESE: 1 g
glycoside alkyl ether sold at 60% AS concentration under the name "TRITON CG 110" by SEPPIC: 5 g AS
spontaneous pH: 6.5
water: qs: 100 g.

The hair is exposed for 15 minutes. After rinsing with water, a hydrogen peroxide composition B is applied, rubbing the hair for 5 minutes.

Composition B containing 12.5 volume hydrogen peroxide hydrogen peroxide: 3.75 g
ammonium lauryl sulphate: 6.7 g
gum arabic: 1 g
stabilizer: 0.03 g
perfume: qs
2-amino-2-methylpropan-1-ol qs: pH 4
water qs: 100 g.

After rinsing the hair with water and drying, a black colour is obtained.

EXAMPLE 9

The colouring of 90% white hair is carried out by applying successively, and rinsing between the two applications, a composition A as follows:

5,6-dihydroxyindole: 2.5 g
potassium iodide: 2 g
propylene glycol: 7 g
guar gum sold under the name "JAGUAR HP 60" by CELANESE: 1 g
glycoside alkyl ether sold at 60% AS concentration under the name "TRITON CG 110" by SEPPIC: 5 g AS
spontaneous pH: 6.5
water qs: 100 g.

The hair is exposed for 15 minutes. After rinsing with water, the composition B, described in Example 8, is applied, rubbing the hair for 5 minutes.

After rinsing the hair with water and drying, a black colour is obtained.

EXAMPLE 10

The colouring of 90% white hair is carried out by applying successively two compositions and rinsing between the two applications.

Composition A below is applied:
5,6-dihydroxyindole: 1.5 g
sodium iodide: 1.5 g
propylene glycol: 7 g
xanthan gum sold under the name "RHODOPOL 23 SC" by RHONE POULENC: 1 g
glycoside alkyl ether sold at 60% AS concentration under the name "TRITON CG 110 by SEPPIC: 5 g AS
water qs: 100 g
spontaneous pH: 6.

The hair is exposed for 15 minutes. After rinsing with water, a 20 volume hydrogen peroxide solution with a pH of 4 is applied, rubbing the hair for 5 minutes.

After rinsing and drying, a black colour is obtained.

EXAMPLE 11

The colouring of natural 90% white hair is carried out by applying successively two compositions and rinsing between the two applications.

The hair is impregnated for 5 minutes with the following composition:
5,6-dihydroxyindole: 2 g
potassium iodide: 2 g
ethyl alcohol: 10 g
water qs: 100 g
spontaneous pH: 4.5.

The hair is rinsed with water and a 20 volume hydrogen peroxide solution with a pH of 3 is then applied, rubbing the hair for 5 minutes. The hair is rinsed with water and a black colour is obtained.

EXAMPLE 12

The colouring of natural 90% white hair is carried out by applying successively two compositions and rinsing between the two applications.

The hair is impregnated for 5 minutes with a 20 volume hydrogen peroxide solution with a pH of 3. The hair is rinsed with water and the following composition is applied:
5,6-dihydroxyindole: 2 g
potassium iodide: 2 g
ethyl alcohol: 10 g
water qs: 100 g
spontaneous pH: 4.5.

The hair is exposed for 5 minutes. After rinsing with water and drying, the hair is dyed medium grey.

EXAMPLE 13

Example 12 is repeated without carrying out an intermediate rinsing between the two applications.
The hair is dyed dark grey.

EXAMPLE 14

Example 11 is repeated without carrying out an intermediate rinsing between the two applications.
The hair is dyed black.

EXAMPLE 15

The colouring of natural 90% white hair is carried out by applying successively two compositions and rinsing between the two applications.

The hair is impregnated for 5 minutes with a composition B containing 20 volume hydrogen peroxide at pH 4. The hair is rinsed with water and the composition A below is applied:
5,6-dihydroxyindole: 1.5 g
ammonium iodide: 1.5 g
ethyl alcohol: 10 g
xanthan gum sold under the name "RHODOPOL 23 SC" by RHONE POULENC: 2 g
glycoside alkyl ether sold at 60% AS concentration under the name "TRITON CG 110" by SEPPIC: 2.1 g AS
water qs: 100 g
spontaneous pH: 5.4.

The hair is exposed for 15 minutes. After rinsing with water and drying, the hair is dyed medium grey.

EXAMPLE 16

Example 15 is repeated, but without rinsing between the two applications of compositions B and A.

A golden dark blond colour is obtained.

EXAMPLE 17

The colouring of 90% white hair is carried out by applying successively two compositions, without rinsing rinsing between the two applications.

The following composition A is applied to the hair and the hair is exposed for 25 minutes.

Composition A:
5,6-dihydroxyindole: 0.1 g
potassium iodide: 0.13 g
ethylene glycol monoethyl ether: 4 g
water: qs 100 g
citric acid: qs pH: 3.5.

A composition B containing 5 volume hydrogen peroxide with a pH of 5 is applied consecutively and without rinsing, and the hair is exposed for 15 minutes.

After rinsing the hair with water and drying, a medium grey colour is obtained.

EXAMPLE 18

The colouring of 90% white, permed hair is carried out by applying successively and rinsing between the two applications, a composition A as follows:
5,6-dihydroxyindole: 0.5 g
potassium iodide: 0.65 g
isopropyl alcohol: 5 g
water: qs 100 g
citric acid: qs pH: 4.

The hair is exposed for 20 minutes. After rinsing with water, a composition B containing 30 volume hydrogen peroxide with a pH of 6 is applied and the hair is exposed for 15 minutes.

After rinsing the hair with water and drying, a natural very dark chestnut brown colour is obtained.

EXAMPLE 19

The colouring of natural 90% white hair is carried out by applying successively two compositions, without rinsing between the two applications.

The hair is impregnated for 2 minutes with a 40 volume hydrogen peroxide composition with a pH of 3.2.

The following composition is then applied and the hair is exposed for 2 minutes:
5,6-dihydroxyindole: 5 g
sodium iodide: 4.7 g
methyl lactate: 8 g
water: qs 100 g
triethanolamine: qs pH: 7.

After rinsing with water and drying, the hair is dyed very dark grey.

EXAMPLE 20

The colouring of strongly bleached hair is carried out by applying successively two compositions A and B, without rinsing between the two applications:

Composition A:
5,6-dihydroxyindole: 0.03 g
potassium iodide: 0.065 g
propan-1-ol: 1 g
water: qs 100 g
citric acid: qs pH: 3.5.

The hair is impregnated for 40 minutes with composition A. A composition B containing 7.5 volume hydrogen peroxide with a pH of 5 is then applied and the hair is exposed for 12 minutes.

After rinsing the hair with water and drying, a light ash blond colour is obtained.

EXAMPLE 21

The colouring of strongly bleached hair is carried out by applying successively two compositions packaged in a dyeing "kit" with 3 compartments, the application of the two compositions A and B being separated by a rinsing with water.

Composition A:
5,6-dihydroxyindole: 3.5 g
sodium iodide: 3.6 g
propylene glycol: 15 g
water: qs 100 g
pH: 2.

Composition B:
7.5 volume hydrogen peroxide with a pH of 5: 100 g.

Composition A is prepared at the time of use by mixing the contents of the two compartments of the "kit" containing respectively:
in one:
5,6-dihydroxyindole: 3.5 g
propylene glycol: 15 g.
in the other:
sodium iodide: 3.6 g
water: 77.9 g
pH: 1.

The hair is exposed to composition A for 10 minutes. Cmposition B is then applied for 7 minutes, without rinsing.

After rinsing with water and drying, a black colour is obtained.

EXAMPLE 22

The dyeing of mink hair is carried out.

Composition A:
5,6-dihydroxyindole: 1 g
potassium iodide: 1 g
ethyl alcohol: 2 g
aqueous sodium chloride solution at the concentration of 30 g/l: 40 g
pH: 6.4.

Composition B:
aqueous 12.5 volume $H_2O_2$ solution: 40 g
pH: 2.4.

A 3.6 piece of mink fur is immersed in composition A at ambient temperature for 15 minutes.

The fur is rinsed with water (temperature: 20° to 25° C.), and it is then immersed in composition B for 5 minutes.

After rinsing and drying, the mink fur, originally chestnut brown, is dyed black. The fur is shiny and soft to touch.

EXAMPLE 23

The dyeing of wool fibres is carried out.

Composition A:
5,6-dihydroxyindole: 2.5 g
potassium iodide: 2.5 g
ethyl alcohol: 10 g
water: qs 100 g
pH: 6.5.

Composition B:
aqueous 12.5 volume $H_2O_2$ solution: 100 g.

The wool fibres are immersed in composition A at ambient temperature for 15 minutes. The fibres are rinsed with water (temperature: 20° to 25° C.), and they are then immersed in composition B for 5 minutes.

After rinsing and drying, the wool fibres, originally white, are dyed black.

We claim:

1. A plural stage process for dyeing keratinous fibers comprising applying to said keratinous fibers in an amount effective to dye said keratinous fibers a composition (A) comprising, in a medium suitable for dyeing keratinous fibers, 5,6-dihydroxyindole present in an amount ranging from 0.01 to 5 weight percent and iodide ions present in an amount ranging from 0.007 to 4 weight percent expressed as $I^-$ ions relative to the total weight of said composition (A), the application of said composition (A) being preceded or followed by the application of composition (B) comprising, in a medium suitable for dyeing keratinous fibers, hydrogen peroxide at a concentration ranging from 1 to 40 volumes at a pH ranging from 2 to 7.

2. The process of claim 1 wherein said composition (B) has a pH ranging from 2 to 5.

3. The process of claim 1 wherein said 5,6-dihydroxyindole is present in an amount ranging from 0.03 to 3 weight percent.

4. The process of claim 1 wherein said iodide ions are present in an amount ranging from 0.008 to 2.5 weight percent.

5. The process of claim 1 wherein said hydrogen peroxide is present at a concentration ranging from 2 to 20 volumes.

6. The process of claim 1 wherein the source of said iodide ions is selected from the group consisting of an alkali metal iodide, an alkaline earth metal iodide and an ammonium iodide.

7. The process of claim 1 wherein said composition (A) is applied to said keratinous fibers in a first stage, said iodide ions being in the form of an iodide selected from the group consisting of an alkali metal iodide, an alkaline earth metal iodide and an ammonium iodide and said composition (B) is applied to said keratinous fibers in a second stage.

8. The process of claim 1 wherein the application of said compositions (A) and (B) is separated by a rinsing stage.

9. The process of claim 1 which is carried out without a rinsing stage between the application of compositions (A) and (B).

10. The process of claim 1 wherein the weight ratio between said 5,6-dihydroxyindole and said iodide ions in composition (A) ranges from 0.05 to 10.

11. The process of claim 10 wherein the weight ratio between said 5,6-dihydroxyindole and said iodide ions in composition (A) ranges from 0.5 to 2.

12. The process of claim 1 wherein compositions (A) and (B) are applied to said keratinous fibers with an exposure time ranging from 10 seconds to 45 minutes.

13. The process of claim 12 wherein the pH of composition (A) ranges from 2 to 7.

14. The process of claim 12 wherein the pH of composition (A) ranges from 3.5 to 7.

15. The process of claim 12 wherein said exposure time ranges from 2 to 20 minutes.

16. The process of claim 1 wherein said medium suitable for dyeing keratinous fibers is water or a water-organic solvent mixture.

17. The process of claim 16 wherein said organic solvent is selected from the group consisting of ethyl alcohol, propyl alcohol, isopropyl alcohol, tert.butyl alcohol, ethylene glycol, the monomethyl ether of ethylene glycol, the monoethyl ether of ethylene glycol, the monobutyl ether of ethylene glycol, ethylene glycol monoethyl ether acetate, propylene glycol, monomethyl ether of propylene glycol, monomethyl ether of dipropylene glycol and methyl lactate.

18. The process of claim 1 wherein compositions (A) and (B) contain at least one adjuvant selected from
 (a) a fatty amide present in an amount ranging from 0.05 to 10 weight percent,
 (b) an anionic, cationic, nonionic or amphoteric surfactant, or a mixture thereof, present in an amount ranging from 0.1 to 50 weight percent,
 (c) a thickening agent present in an amount ranging from 0.1 to 5 weight percent and selected from the group consisting of sodium alginate, gum arabic, guar gum, xanthan gum, a scleroglucan, methyl cellulose, hydroxyethyl cellulose, hydroxypropylmethyl cellulose, sodium salt of carboxymethyl cellulose, acrylic acid polymer and bentonite,
 (d) a perfume,
 (e) a sequesterant,
 (f) a film forming agent,
 (g) a dispersant,
 (h) a conditioner,
 (i) a preservative,
 (j) an opacifier and
 (k) a swelling agent.

19. The process of claim 1 wherein said keratinous fibers are human hair.

20. A keratinous fiber dyeing composition comprising, in a medium suitable for dyeing keratinous fibers, 5,6-dihydroxyindole present in an amount ranging from 0.01 to 5 weight percent and iodide ions present in an amount ranging from 0.007 to 4 weight percent expressed in $I^-$ ions relative to the total weight of said composition.

21. The composition of claim 20 wherein said 5,6-dihydroxyindole is present in an amount ranging from 0.03 to 3 weight percent.

22. The composition of claim 20 wherein said iodide ions are present in an amount ranging from 0.008 to 2.5 weight percent.

23. The composition of claim 20 wherein said iodide ions are in the form of an iodide selected from the group consisting of an alkalimetal iodide, an alkaline earth metal iodide and an ammonium iodide.

24. The composition of claim 20 wherein said medium is an aqueous medium and said composition has a pH ranging from 2 to 7.

25. The composition of claim 24 having a pH ranging from 3.5 to 7.

26. The composition of claim 20 wherein said medium is an anhydrous solvent medium.

27. A kit for dyeing keratinous fibers containing at least two compartments, one of said compartments containing a composition comprising in a medium suitable for dyeing keratinous fibers, 5,6-dihydroxyindole present in an amount ranging from 0.01 to 5 weight percent and iodide ions present in an amount ranging from 0.007 to 4 weight percent expressed as $I^-$ ions relative to the total weight of said composition, and another of said compartments containing an aqueous composition of hydrogen peroxide present at a concentration of 1 to 40 volumes, said aqueous composition having a pH ranging from 2 to 7.

28. The kit of claim 27 wherein the medium suitable for dyeing keratinous fibers present in said one compartment is an aqueous medium and has a pH ranging from 2 to 7.

29. A kit for dyeing keratinous fibers containing at least three compartments, a first of said compartments containing a composition comprising in a medium suitable for dyeing keratinous fibers iodide ions present in an amount ranging from 0.007 to 4 weight percent expressed as I$^-$ ions, a second of said compartments containing a composition comprising, in a medium suitable for dyeing keratinous fibers, 5,6-dihydroxyindole present in an amount ranging from 0.01 to 5 weight percent, and a third of said compartments containing an aqueous composition of hydrogen peroxide present at a concentration of 1 to 40 volumes, said aqueous composition having a pH ranging from 2 to 7.

30. The kit of claim 29 wherein the medium suitable for dyeing keratinous fibers in each of said first and second of said compartments is an aqueous medium, the aqueous medium in said first of said compartments having a pH ranging from 2 to 11 and the aqueous medium in said second of said compartments having a pH ranging from 2 to 7.

* * * * *